(12) United States Patent
Pazzuconi et al.

(10) Patent No.: US 7,241,931 B2
(45) Date of Patent: Jul. 10, 2007

(54) PROCESS FOR THE PREPARATION OF 2,6-DIMETHYLNAPHTHALENE

(75) Inventors: Giannino Pazzuconi, Broni (IT); Carlo Perego, Carnate (IT); Giuseppe Bellussi, Piacenza (IT)

(73) Assignees: Enichem S.p.A., San Donato Milanese (IT); ENI S.p.A., Rome (IT); Enitechnologie S.p.A., San Donato Milanese (IT)

( * ) Notice: Subject to any disclaimer, the term of this patent is extended or adjusted under 35 U.S.C. 154(b) by 0 days.

(21) Appl. No.: 11/333,201

(22) Filed: Jan. 18, 2006

(65) Prior Publication Data

US 2006/0122445 A1 Jun. 8, 2006

Related U.S. Application Data

(62) Division of application No. 10/357,379, filed on Feb. 4, 2003, now Pat. No. 7,019,186, which is a division of application No. 09/690,011, filed on Oct. 17, 2000, now abandoned.

(30) Foreign Application Priority Data

Oct. 18, 1999 (IT) .............................. MI99A2171

(51) Int. Cl.
C07C 5/22 (2006.01)
C07C 5/27 (2006.01)

(52) U.S. Cl. ...................... 585/481; 585/480

(58) Field of Classification Search ............... 585/481, 585/480

See application file for complete search history.

(56) References Cited

U.S. PATENT DOCUMENTS

| | | | |
|---|---|---|---|
| 3,832,449 A | 8/1974 | Rosinski et al. | |
| 3,962,364 A | 6/1976 | Young | |
| 3,972,832 A | 8/1976 | Butter et al. | |
| 4,002,698 A | 1/1977 | Kaeding | |
| 4,088,706 A | 5/1978 | Kaeding | |
| 4,402,867 A | 9/1983 | Rodewald | |
| 4,421,941 A | 12/1983 | Olson et al. | |
| 4,590,321 A | 5/1986 | Chu | |
| 4,605,804 A | 8/1986 | Chang et al. | |
| 5,981,418 A | 11/1999 | Drake et al. | |
| 6,048,816 A | 4/2000 | Brown et al. | |
| 6,147,270 A | 11/2000 | Pazzuconi et al. | |
| 6,187,982 B1 | 2/2001 | Beck et al. | |
| 6,232,517 B1 | 5/2001 | Pazzuconi et al. | |
| 7,019,186 B2 | 3/2006 | Pazzuconi et al. | |
| 2003/0069459 A1 | 4/2003 | Girotti et al. | |

FOREIGN PATENT DOCUMENTS

| | | |
|---|---|---|
| EP | 0 296 582 | 12/1988 |
| EP | 0 621 251 | 10/1994 |
| EP | 0 950 650 | 10/1999 |
| EP | 1 069 102 | 1/2001 |
| GB | 2 246 788 | 2/1992 |
| WO | WO 90/03960 | 4/1990 |
| WO | WO 98/41595 | 9/1998 |

*Primary Examiner*—Thuan Dinh Dang
(74) *Attorney, Agent, or Firm*—Oblon, Spivak, McClelland, Maier & Neustadt, P.C.

(57) ABSTRACT

A highly selective process is described for preparing 2,6-dimethylnaphthalene which comprises reacting a naphthalene hydrocarbon selected from naphthalene, methylnaphthalenes, dimethylnaphthalenes, trimethylnaphthalenes, polymethylnaphthalenes, and/or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions and in the presence of a catalytic composition comprising a zeolite belonging to the MTW structural type and at least one element selected from P, B and Si. The process is preferably carried out in the presence of a methylating agent.

2 Claims, No Drawings

PROCESS FOR THE PREPARATION OF 2,6-DIMETHYLNAPHTHALENE

A highly selective process is described for preparing 2,6-dimethylnaphthalene which comprises reacting a naphthalene hydrocarbon selected from naphthalene, methylnaphthalenes, dimethylnaphthalenes, trimethylnaphthalenes, polymethylnaphthalenes, or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions and in the presence of a catalytic composition comprising a zeolite belonging to the MTW structural type and at least one element selected from P, B and Si. The process is preferably carried out in the presence of a methylating agent.

2,6-dimethylnaphthalene is an intermediate in the synthesis of 2,6-naphthalenedicarboxylic acid, used as monomer in the preparation of PEN (polyethylnaphthalate). It is known that it can be recovered from fractions coming from the reforming of kerosene (U.S. Pat. No. 4,963,248) or FCC oil fractions (European Chemical News, page 30, 28.09.1992). In the former case, the dimethylnaphthalenes must be separated by distillation and the 2,6 isomer is subsequently isolated by means of selective absorptions and/or crystallization. In the latter case there is a further problem due to the presence of nitrogen and sulfur which poison the catalysts used for the separation and/or isomerization phases. There is also a process (U.S. Pat. No. 4,990,717; U.S. Pat. No. 5,118,892; U.S. Pat. Nos. 5,073,670; 5,030,781; 5,012,024) for the selective synthesis of 2,6-dimethylnaphthalene by means of a series of alkenylation, cyclization, dehydrogenation, isomerization processes. Such a high number of passages is obviously extremely costly and in addition each passage or chemical reaction involves secondary reactions requiring separation to guarantee the purity of the intermediates or end-product.

U.S. Pat. No. 5,043,501 describes a synthesis method of 2,6-dimethylnaphthalene in two steps. The first comprises the alkylation of an alkylaromatic with a $C_5$ olefin in the presence of a zeolitic catalyst, the second step includes dehydrocyclization at 400–500° C. with a catalyst consisting of Pt/Ba/K on L zeolite, obtaining a product containing dimethylnaphthalenes which are then isomerized mainly to 2,6 isomer.

In Applied Catalysis A, General 146 (1996) 305–316, S. B. Pu and T. Inui describe the alkylation of methylnaphthalene with methanol, catalyzed by zeolites of the BEA, FAU and MTW group, carried out without a solvent and in exclusively gaseous phase. The best results are obtained with beta zeolite and faujasite. A. S. Loktev and P. S. Chekriy, in Zeolites and Related Microporous Materials: State of Art 1994, SSSC vol. 84, J. Weitkamp et al. (Eds) describe the alkylation of naphthalene or methylnaphthalene with methanol catalyzed by ZSM-12, carried out in the presence of paraffinic solvents and in gaseous phase. The yields to dimethylnaphthalenes, and 2,6 isomer in particular, are zero or negligible. Furthermore, significant quantities of heavy by-products are obtained, due to the reaction and/or decomposition conditions of the paraffinic solvents used.

U.S. Pat. No. 4,795,847 describes a process for the preparation of 2,6-dialkylnaphthalenes which comprises the alkylation in gas phase of naphthalene or 2-alkyl-naphthalene with an alkylating agent in the presence of a zeolite selected from mordenite, EU-1, offretite, ZSM-12, ZSM-5 and ZSM-22. In the case of the methylation of naphthalene or 2-methylnaphthalene, the use of ZSM-5 zeolite is particularly preferred. In order to reduce undesired isomerization reactions which cause the formation of 1-alkyl-naphthalene, the zeolitic catalyst is previously subjected to a precarbonization treatment. An illustration is provided of the alkylation of 2-methylnaphthalene with methanol, in gas phase, catalyzed by ZSM-5: the conversion obtained between 0.5 and 8 hours ranges from 5 to 7%, the yield to dimethylnaphthalenes ranges from 4 to 5% and the 2,6-dimethylnaphthalene isomer forms 50% of the dimethylnaphthalene fraction.

Italian patent application MI98A000809 describes a process for preparing 2,6-dimethylnaphthalene by the reaction of naphthalene, methylnaphthalenes, dimethylnaphthalenes, trimethylnaphthalenes and/or polymethylnaphthalenes with one or more benzene hydrocarbons selected from benzene, toluene, xylenes, trimethylbenzenes, tetramethylbenzenes, pentamethylbenzene and hexamethylbenzene, carried out under at least partially liquid phase conditions and in the presence of a zeolite belonging to the MTW structural type and optionally in the presence of a methylating agent. This process allows better results to be obtained in terms of yield, selectivity, conversion to useful products in the time unit and catalyst life, with respect to what is described in the prior art. MTW zeolites in particular, under the conditions described in MI98A000809, prove to be more active than the same zeolites used according to the conditions described in prior documents, and also with respect to BEA and MFI zeolites already described in the known art as the best catalysts for the preparation of 2,6-dimethylnaphthalene. Zeolites of the MTW structural type which can be used in said invention are for example: ZSM-12, CZH-5, Nu-13, Theta-3 and TPZ-12. The CZH-5 zeolite is described in GB 207,9735A; Nu-1 is described in EP 59059; Theta-3 is described in EP 162,719 and TPZ-12 in U.S. Pat. No. 4,557,919. The MTW structural type zeolite preferably used in MI98A000809 is a silicoaluminate with a molar ratio $SiO_2/Al_2O_3$ greater than or equal to 20. This zeolite is described in A. Katovic and G. Giordano, Chem. Ind. (Dekker) (Synthesis of Porous Materials) 1997 69, 127–137. The aluminum can be totally or partly substituted by B, Ga, Fe or their mixtures, as described by Toktarev & Ione, in Chon et al., Progress in Zeolites and Microporous Material, SSSC, vol. 105, 1997. According to a preferred aspect of patent application MI98A000809, ZSM-12 zeolite is used, a porous crystalline material having, in its calcined and anhydrous form, a molar composition of oxides corresponding to the following formula:

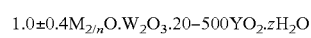

$$1.0 \pm 0.4 M_{2/n}O \cdot W_2O_3 \cdot 20-500 YO_2 \cdot zH_2O$$

wherein M is $H^+$ and/or a cation of an alkaline or earthalkaline metal with a valence n, W is selected from aluminum, gallium or their mixtures, Y is selected from silicon and germanium, z ranges from 0 to 60. M is preferably selected from sodium, potassium, hydrogen or their mixtures. W is preferably aluminum and Y is preferably silicon. W can be at least partially substituted by boron, iron or their mixtures. ZSM-12 zeolite is described in U.S. Pat. No. 3,832,449, in Ernst et al., Zeolites, 1987, Vol. 7, September, and in Toktarev & Ione, Chon et al., Progress in Zeolites and Microporous Material, SSSC, Vol. 105, 1997. The MTW zeolite is preferably used in the form in which the cationic sites present in its structure are occupied by at least 50% of hydrogen ions. It is especially preferred for at least 90% of the cationic sites to be occupied by hydrogen ions.

In the process for preparing the 2,6-dimethylnaphthalene of Italian patent application MI98A000809, the feeding of the benzene hydrocarbon is such as to obtain a molar ratio between said hydrocarbon and the naphthalene groups ranging from 1 to 100, more preferably from 3 to 20, wherein naphthalene groups refers to the naphthalene hydrocarbon used as substrate or, when several naphthalene hydrocarbons are present, the sum of their moles. When the process of said invention is carried out in the presence of a methylating agent, a molar ratio between methylating agent and naphthalene groups of less than 30, preferably between 0.1 and 3, is used. The naphthalene hydrocarbon is preferably selected from naphthalene, methylnaphthalenes, dimethylnaphthalenes and their mixtures. A particularly preferred aspect is for the reagent to be naphthalene and/or methylnaphthalene, optionally mixed with dimethylnaphthalenes and/or trimethylnaphthalenes. The benzene hydrocarbon preferably used is trimethylbenzene. The methylating agent can be selected from methanol, dimethylether, dimethylcarbonate, dimethylsulfate, methyl hydride, and is preferably methanol. The reaction temperature for the process described in said patent application MI98A000809 ranges from 200° C. to 450° C., preferably from 250 to 390° C., even more preferably from 280 to 350° C.; the WHSV space velocity ranges from 0.01 to 8 hours$^{-1}$, preferably from 0.05 to 1 hours$^{-1}$. The combination between the temperature and pressure conditions used should be such as to guarantee that the process takes place in at least partially liquid phase. The pressure used can range from 3 to 60 atm.

The naphthalene hydrocarbon(s) used as substrate in the synthesis process of 2,6-dimethylnaphthalene described in Italian patent application MI98A000809 can be contained in naphthalene cuts obtained by the fractionation of appropriate petrochemical streams and subsequent treatment of the product deriving from the fractionation with solid acid, as described in Italian patent application MI 99A001533. In fact, object of said Italian patent application MI 99A001533, filed on Jul. 13, 1999 by the same Applicant, relates to the use, in the synthesis of 2,6-dimethylnaphthalene, of a naphthalene cut obtained by the fractionation of petrochemical streams and subsequent acid treatment of the product thus obtained, and a process is then described and claimed for the preparation of 2,6-dimethylnaphthalene comprising reacting, with the aromatic hydrocarbon selected from benzene, toluene, xylenes, tetramethylbenzenes, pentamethylbenzene, hexamethylbenzene or their mixtures, under at least partially liquid phase conditions and in the presence of MTW zeolite and optionally in the presence of a methylating agent, a mixture of naphthalenes comprising a cut obtained by the fractionation of suitable petrochemical streams and subsequent treatment of the naphthalene cut thus obtained with a solid acid.

Petrochemical streams which can be used are FOK (Fuel Oil Cracking), LCO (Light Cycle Oil) and heavy fractions from catalytic reforming which contain significant and relatively "clean" quantities of naphthalene, which at present are not fully exploited (for example FOK, in certain cases, is used as fuel). They provide an economic source of naphthalenes, which can be separated by distillation. For this purpose, in Italian patent application MI 99A001533, the FOK, LCO petrochemical streams or heavy fractions deriving from catalytic reforming are subjected to fractionation to obtain the cut of interest, which contains at least 20% of useful naphthalenes (mainly naphthalene and methylnaphthalenes), and the cut thus obtained is treated with a solid acid. The treatment can be carried out batchwise or in continuous, and is effected at a temperature varying from room temperature to 360° C., and at such a pressure as to guarantee that the operation takes place in liquid phase. The quantity of solid acid varies, with respect to the liquid to be treated, from 0.1 to 5% by weight; the WHSV (hours$^{-1}$) can range from 0.1 to 6. For this purpose, solid acid materials can be used, either totally or partially acid, such as clays (montmorillonites, smectites . . . ) or their phyllosilicate constituents, zeolites, sulfated zirconia, acid resins (e.g. sulfonic resins), activated and non-activated alumina (optionally chlorinated or fluorinated), acid oxides in general, also in mixtures, amorphous silico-aluminas. Supported acids and heteropolyacids can also be used, such as for example $H_3PO_4$ on kieselguhr. The naphthalene cut resulting from this treatment is then reacted, to prepare 2,6-dimethylnaphthalene, with an aromatic hydrocarbon selected from benzene, toluene, xylenes, tetramethylbenzenes, pentamethylbenzene, hexamethylbenzene or their mixtures, under partially liquid phase conditions, in the presence of MTW zeolite and optionally an alkylating agent, according to the process claimed in patent application MI98A000809 whose contents are described above.

It has now been unexpectedly found that the addition of one or more elements selected from P, B and Si to MTW zeolite allows its catalytic performances to be improved in the synthesis of 2,6-dimethylnaphthalene both in terms of yield and selectivity and conversion to useful products in the time unit. This catalytic composition also has a greater duration than that of MTW zeolite alone.

An object of the present invention therefore relates to a process for preparing 2,6-dimethylnaphthalene which comprises reacting a naphthalene hydrocarbon selected from naphthalene, methylnaphthalenes, dimethylnaphthalenes, trimethylnaphthalenes, tetramethylnaphthalenes, pentamethylnaphthalenes, hexamethylnaphthalenes and/or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions and in the presence of a catalytic composition comprising a zeolite belonging to the MTW structural type and at least one element A selected from P, B and Si, said process being optionally carried out in the presence of a methylating agent.

MTW structural type zeolites which can be used in the catalytic composition of the present invention are for example: ZSM-12, CZH-5, Nu-13, Theta-3 and TPZ-12.

CZH-5 zeolite is described in GB 207,9735A; Nu-1 is described in EP 59059; Theta-3 is described in EP 162,719 and TPZ-12 in U.S. Pat. No. 4,557,919.

The MTW structural type zeolite which is most suitable for use in the present invention is a silico-aluminate with a molar ratio $SiO_2/Al_2O_3$ greater than or equal to 20.

This zeolite and its preparation are described in A. Katovic and G. Giordano, Chem. Ind. (Dekker) (Synthesis of Porous Materials) 1997 69, 127–137. The aluminum can be totally or partially substituted by B, Ga, Fe or their mixtures as described by Toktarev & Ione, in Chon et al., Progress in Zeolites and Microporous Materials, SSSC, vol. 105, 1997.

According to a preferred aspect, ZSM-12 zeolite is used, a porous crystalline material having, in its calcined and anhydrous form, a molar composition of oxides corresponding to the following formula:

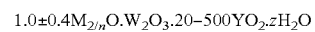

$$1.0 \pm 0.4 M_{2/n}O \cdot W_2O_3 \cdot 20{-}500 YO_2 \cdot zH_2O$$

wherein M is $H^+$ and/or a cation of an alkaline or earthalkaline metal with a valence n, W is selected from aluminum, gallium or their mixtures, Y is selected from silicon and germanium, z ranges from 0 to 60. M is preferably selected from sodium, potassium, hydrogen or their mixtures. W is preferably aluminum and Y is preferably silicon. W can be at least partially substituted by boron, iron or their mixtures. ZSM-12 zeolite is described in U.S. Pat. No. 3,832,449, in Ernst et al., Zeolites, 1987, Vol. 7, September, and in Toktarev & Ione, Chon et al., Progress in Zeolites and Microporous Material, SSSC, Vol. 105, 1997.

A particularly preferred aspect of the present invention is that in the catalytic composition, the MTW zeolite is in the form in which the cationic sites present in its structure are occupied by at least 50% of hydrogen ions. It is especially preferred for at least 90% of the cationic sites to be occupied by hydrogen ions.

Si, P and/or B are introduced into the catalytic composition by means of treatment of the MTW zeolite, preferably in ammonia form, with a compound of Si, P and/or B using any of the known techniques, such as mechanical mixing, impregnation or deposition in vapor phase. The Si, P and/or B compound can be selected from the corresponding salts, acids and organic compounds. Compounds which can be used are: silicic acids, phosphorous acids, silicon alkoxides, phosphorous alkoxides and boron alkoxides.

The catalytic composition is preferably prepared using the known impregnation technique, i.e. by treating the zeolite, preferably in ammonia form, with an aqueous solution of a compound of Si, P and/or B. The resulting suspension, after being maintained under stirring, is dried under vacuum at a temperature which is sufficient to eliminate the solvent. The operating procedure and conditions of the impregnation are known to experts in the field. The solid remaining after drying is subsequently calcined at a temperature ranging from 400 to 600° C. for 1–10 hours.

A preferred aspect is for the element A to be phosphorous. The weight quantity of the element(s) A is preferably less than 3% with respect to the total weight of the catalytic composition and is even more preferably greater than or equal to 0.05% and less than or equal to 2% with respect to the total weight of the catalytic composition.

The catalytic composition can be used as such, pelletized in pure form, or extruded with suitable inorganic oxide binders to form cylindrical, spherical pellets, or pellets having other forms commonly used, or obtained in the form of microspheres by spray-drying after mixing with a binder. The binders can be for example aluminas, silicas, silico-aluminas, titania, zirconia or clays. Alumina is preferably used. In the bound catalyst, the catalytic composition and binder are in a weight ratio ranging from 10:90 to 90:10, preferably from 25:75 to 75:25.

The naphthalene hydrocarbon used in the process of the present invention is preferably selected from naphthalene, methylnaphthalenes, dimethylnaphthalenes, trimethylnaphthalenes or their mixtures. A particularly preferred aspect is for the reagent to be naphthalene and/or methylnaphthalene, optionally mixed with dimethylnaphthalenes and/or trimethylnaphthalenes.

The benzene hydrocarbon used is preferably trimethylbenzene.

According to a particularly preferred aspect of the present invention, the process for the preparation of 2,6-dimethylnaphthalene is carried out in the presence of the methylating agent, which can be selected from methanol, dimethylether, dimethylcarbonate, dimethylsulfate, methyl hydride. Methanol is preferably used.

Operating according to our invention, an improvement is unexpectedly obtained both in terms of yield and selectivity and conversion to useful products in the time unit, with respect to the results obtained using MTW zeolite alone as catalyst. Compared to zeolites of the MTW group, the catalytic compositions containing zeolites of the MTW structural type and at least one element A selected from P, Si and B, provide better results not only because they are more active, with a longer life and consequently greater productivity, but also because they provide a product containing a higher percentage of 1,6 and 1,5 isomers, easily convertible to 2,6 isomer, by means of commercial processes or known methods such as those described for example in EP 519,165 and U.S. Pat. No. 5,012,024.

In addition, with the catalytic composition of the present invention, a better molar ratio is obtained between 2,6 and 2,7 isomers of dimethylnaphthalene with respect to the results obtained using MTW zeolite alone as catalyst. As is known to experts in the field, it is difficult to separate 2,6-dimethylnaphthalene from the other isomers using the conventional separation methods such as distillation or crystallization, mainly owing to the presence of 2,7-dimethylnaphthalene. In distillation, 2,6 and 2,7-dimethylnaphthalene cannot be separated from each other as the difference in their boiling points is only 0.3° C. In crystallization, as the 2,6 isomer and 2,7 isomer form a eutectic mixture with a 2,6/2,7 ratio=0.7 (as described in EP 0889016), the separation normally causes a low yield to 2,6 isomer. The thermodynamic equilibrium involves a ratio between these two isomers of about 1 (S. B. Pu & T. Inui, Applied Catalysis A Gen 146 (1996) 305–316). As a result of this, there are usually low yields of 2,6-dimethylnaphthalene in the separation phase.

Another advantageous aspect of the process of the present invention is therefore the higher selectivity in the formation of the 2,6 isomer and with a molar ratio 2,6 isomer/2,7 isomer even more unbalanced towards the 2,6 isomer which allows the yields to be improved in the fractionated crystallization phase.

The process of the present invention is the result of contemporary transalkylation, deproportioning, isomerization and alkylation reactions in which all the types of methyl present in the reaction mixture unexpectedly participate, either directly or indirectly, in the methylation of the naphthalene substrate used, contributing to the production of extremely high selectivities. Methyls present in the reaction mixture refer both to those deriving from the benzene hydrocarbon and to those possibly already present on one or more of the naphthalene substrates used.

In accordance with this, at the end of the process, the benzene hydrocarbon or mixture of benzene hydrocarbons used, will produce a mixture of the corresponding benzene hydrocarbons quantitatively and qualitatively variously methylated, deriving from the processes specified above. The best results are obtained when operating in the presence of the methylating agent and consequently at least part of the methyls contained in the 2,6-dimethylnaphthalene derive directly therefrom or indirectly, i.e. by alkylation on the part of the methylating agent of the aromatic hydrocarbon and subsequent transalkylation on the naphthalene substrate.

The feeding of the benzene hydrocarbon is such as to obtain a molar ratio between said hydrocarbon and the naphthalene groups ranging from 1 to 100, more preferably from 3 to 20, naphthalene groups referring to the naphthalene hydrocarbon used as substrate or, when several naphthalene hydrocarbons are present, the sum of their moles.

When the process of the present invention is carried out in the presence of a methylating agent, preferably methanol, a molar ratio between methylating agent and naphthalene groups of less than 30, preferably from 0.1 to 3, is used.

It is obviously necessary to operate in the presence of the methylating agent when benzene alone is used as benzene hydrocarbon together with naphthalene alone as naphthalene substrate.

The reaction temperature ranges from 200° C. to 450° C., preferably from 250 to 390° C., even more preferably from 280 to 350° C.; the WHSV space velocity ranges from 0.01 to 8 hours$^{-1}$, preferably from 0.05 to 1 hours$^{-1}$.

It should be pointed out that the combination of temperature and pressure conditions used should be such as to guarantee that the synthesis of 2,6-dimethylnaphthalene takes place at least partially in liquid phase, and even more preferably takes place substantially in liquid phase. The pressure used can range from 3 to 60 atm.

The process of the present invention can be industrially carried out in continuous, in semi-continuous or batchwise; in order to maintain the temperature within the preferred range, the catalyst can be arranged in the reactor in various layers. A quench with naphthalene, with the hydrocarbon or mixture of benzene hydrocarbons used in the process itself, or with the methylating agent, preferably methanol, when present, can be carried out between one layer and another.

The temperature control can be effected not only by means of a quench of reagents and/or inert products, but also by inter-cooling between the layers, for example by the interposition of coolers. The synthesis of 2,6-dimethylnaphthalene can be suitably carried out either in a reactor in which the catalyst is arranged in two or more beds or in two or more reactors in series, inter-cooled to control the temperature.

When an alkylating agent is used, this can be fed in two or more steps. The alkylating agent is preferably fed in two or more steps along the catalytic beds of the reactor or between these, and/or between the reactors situated in series.

Naphthalene cuts obtained by the fractionation of petrochemical streams, and especially naphthalene cuts obtained by the fractionation of petrochemical streams and treated with a solid acid as described in Italian patent application MI 99/A 001533 filed by the same Applicant, whose contents are described above, can be used as substrates for the process of the present invention, which contain the naphthalene hydrocarbon(s).

A further object of the present invention therefore relates to a process for the preparation of 2,6-dimethylnaphthalene comprising the following steps:
fractionation of a suitable petrochemical stream;
treatment of the naphthalene cut thus obtained with a solid acid;
sending the product thus obtained for reaction with the aromatic hydrocarbon selected from benzene, toluene, xylene, tetramethylbenzenes, pentamethylbenzene, hexamethylbenzene and/or their mixtures, under at least partially liquid phase conditions, in the presence of a catalytic composition containing MTW zeolite and at least one element A selected from P, Si and B, optionally in the presence of a methylating agent.

Petrochemical streams preferably used are FOK, LCO and heavy fractions from catalytic reforming. Their fractionation to obtain the cut of interest, which contains at least 20% of useful naphthalenes (mainly naphthalene and methylnaphthalenes), is carried out using the conventional distillation methods, for example with a plate column under vacuum.

The naphthalene cut thus obtained is subjected to treatment with a solid acid, which is effected by sending said cut, before feeding to the synthesis of 2,6-dimethylnaphthalene, onto a pre-bed consisting of said solid acid. The treatment can take place batchwise or in continuous, and is carried out at a temperature ranging from room temperature to 360° C., and at such a pressure as to guarantee that the operation takes place in liquid phase. The quantity of solid acid varies, with respect to the liquid to be treated, from 0.1 to 5% by weight; the WHSV (hours$^{-1}$) can vary from 0.1 to 6. Solid acid materials can be used for the purpose, either totally or partially acid, such as clays (e.g. montmorillonites, smectites) or their phyllosilicate constituents, zeolites, sulfated oxides, such as for example sulfated zirconia, acid resins (e.g. sulfonic resins), activated and non-activated alumina (optionally chlorinated or fluorinated), acid oxides in general, also in mixtures, amorphous silico-aluminas. Supported acids and heteropolyacids can also be used, such as for example $H_3PO_4$ on kieselguhr.

The reaction of the treated product thus obtained, with the aromatic hydrocarbon for the preparation of 2,6-dimethylnaphthalene in the presence of the catalytic composition containing the MTW zeolite and at least one element A selected from P, Si and B, is carried out under the conditions described above for the process of the present invention.

According to another preferred aspect of the present invention, in order to maximize the production of 2,6-dimethylnaphthalene, the product obtained at the end of the preparation process can be separated into: (a) a fraction containing benzene hydrocarbons, naphthalene and methylnaphthalene, (b) a fraction containing dimethylnaphthalenes and (c) a fraction containing polymethylated naphthalenes. The desired 2,6-dimethylnaphthalene isomer is isolated from the fraction (b) of dimethylnaphthalenes, whereas the remaining fraction (d), containing dimethylnaphthalenes different from the 2,6 isomer, and fractions (a) and (c), are re-fed to the initial reactor where they enter the reactive cycle. Alternatively, said fraction (d) and fractions (a) and (c), optionally enriched with naphthalene and/or methylnaphthalene, can be fed to a specific reactor where they are reacted, under at least partially liquid phase conditions, in the presence of the catalytic composition containing the MTW zeolite and at least one element A selected from P, Si and B, with one or more benzene hydrocarbons selected from benzene, toluene, xylenes, trimethylbenzenes, tetramethylbenzenes, pentamethylbenzene and/or hexamethylbenzene. The reaction temperature ranges from 200 to 450° C., and the space velocity ranges from 0.01 to 8 hours$^{-1}$.

According to another aspect of the present invention, in order to maximize the production of 2,6-dimethylnaphthalene, the fraction (d) containing dimethylnaphthalenes different from 2,6-dimethylnaphthalene, in particular the 1,6 and 1,5 isomer, is subjected to isomerization, under at least partially liquid phase conditions, in the presence of a catalytic composition containing an MTW zeolite and at least one element A selected from P, Si and B, at a temperature ranging from 100 to 400° C., more preferably from 120 to 250° C., even more preferably from 130 to 200° C.

This particular isomerization process of 1,6-dimethylnaphthalene and 1,5-dimethylnaphthalene, either pure or mixed with other dimethylnaphthalene isomers, to give 2,6-dimethylnaphthalene, catalyzed by the catalytic composition containing an MTW zeolite and at least one element A selected from P, Si and B, is new and is a further object of the present invention. The element A is preferably in a quantity lower than 3%.

The catalytic composition containing a zeolite belonging to the MTW structural type and at least one element A selected from P, B and Si is new and is an additional object of the present invention.

The weight quantity of element(s) A is preferably less than 3% with respect to the total weight of the catalytic composition and is even more preferably greater than or equal to 0.05% and less than or equal to 2% by weight with respect to the total weight of the catalytic composition.

The exhausted catalyst deriving from the process for preparing 2,6-dimethylnaphthalene can be regenerated by means of the known combustion methods of coke or its precursors to which the deactivation of the solid acid materials which catalyze the reactions involving hydrocarbons, is due. We have also found that once this catalyst is exhausted, it can be regenerated in the synthesis reactor of 2,6-dimethylnaphthalene itself, by treatment with one or more of the benzene hydrocarbons used in the synthesis reaction of 2,6-dimethylnaphthalene, at a temperature ranging from 200° to 450° C., more preferably from 250° to 400° C., even more preferably from 280° to 370° C., said temperature being at least equal to that used during the preparation process of 2,6-dimethylnaphthalene from which the exhausted catalyst derives. The regeneration conditions are selected so as to operate in at least partially liquid phase, the WHSV space velocity can range from 0.01 to 8 hours$^{-1}$ and the pressure can be selected from 5 to 60 atm.

EXAMPLE 1

Preparation of a Catalytic Composition Containing MTW Zeolite and 0.5% of P 2.4 grams of sodium aluminate at 56% of $Al_2O_3$ are dissolved in 84 grams of aqueous solution of tetraethylammonium hydroxide at 35%. The limpid solution thus obtained is poured, under stirring, into 200 grams of colloidal silica Ludox HS 40. After brief stirring, a limpid, homogeneous gel is obtained, which is poured into an AISI316 steel autoclave, equipped with an anchor stirrer. The gel is left to crystallize under hydrothermal conditions at 160° C. for about 60 hours.

At this point the autoclave is cooled and the solid separated from the mother liquor and washed with demineralized water until the washing water has a pH of less than 9.

The solid is calcined at 550° C. in an atmosphere of air, for 5 hours. It is then suspended in a solution of demineralized water and ammonium acetate, the latter in an excess molar quantity, in particular 5 times, with respect to the synthesis aluminum formally present. During this operation, the synthesis sodium contained in the zeolite is substituted by the ammonium ion by means of ion exchange. This first exchange is followed by a washing, a second exchange using the same procedure as the first and another washing. The solid is then definitively separated from the aqueous environment and dried, obtaining the zeolite in ammonia form.

10 grams of zeolite in ammonia form are dispersed in 50 grams of demineralized water in which $(NH_4)_2HPO_4$ has been dissolved in a quantity of 0.5% by weight of P with respect to the zeolite, i.e. 0.215 g of salt. The mixture is maintained under stirring for about 30 minutes at approximately 60° C., and is then dried under vacuum. The solid thus obtained is calcined in air for 5 hours at 550° C., thus obtaining the catalyst in completely acid form.

An XRD analysis is carried out on the end-samples, demonstrating the presence of the crystalline MTW-type zeolitic phase alone, together with a chemical analysis on the basis of which the residual sodium proves to be less than 50 ppm and the molar ratio $SiO_2/Al_2O_3$ is 99.

EXAMPLE 2

Preparation of Non-Modified MTW Zeolite 2.4 grams of sodium aluminate at 56% of $Al_2O_3$ are dissolved in 84 grams of aqueous solution of tetraethylammonium hydroxide at 35%. The limpid solution thus obtained is poured, under stirring, into 200 grams of colloidal silica Ludox HS 40. After brief stirring, a limpid, homogeneous gel is obtained, which is poured into an AISI316 steel autoclave, equipped with an anchor stirrer. The gel is left to crystallize under hydrothermal conditions at 160° C. for about 60 hours.

At this point the autoclave is cooled and the solid separated from the mother liquor and washed with demineralized water until the washing water has a pH of less than 9.

The solid is calcined at 550° C. in an atmosphere of air for 5 hours. It is then suspended in a solution of demineralized water and ammonium acetate, the latter in an excess molar quantity, in particular 5 times, with respect to the synthesis aluminum formally present. During this operation, the synthesis sodium present in the zeolite is substituted by the ammonium ion by means of ion exchange. This first exchange is followed by a washing, a second exchange using the same procedure as the first and another washing. The solid is then definitively separated from the aqueous environment and dried, obtaining the zeolite in ammonia form. The solid thus obtained is calcined in air for 5 hours at 550° C., thus obtaining the catalyst in completely acid form.

An XRD analysis is carried out on the end-sample, demonstrating the presence of the crystalline MTW-type zeolitic phase alone, together with a chemical analysis on the basis of which the residual sodium proves to be less than 50 ppm and the molar ratio $SiO_2/Al_2O_3$ is 99.

EXAMPLE 3

Catalytic Test

Two catalytic tests are carried out analogously with the same reagents, using the following procedure.

Four grams of catalyst obtained as described in examples 1 and 2 respectively, transformed into tablets and granulated within a range of 20–40 mesh, are charged into the isothermal zone of a fixed bed reactor, with quartz above and below as inert filler. The temperature of the reactor is brought to 200° C. for at least two hours, under a stream of nitrogen against atmospheric pressure. Under a stream of inert gas, the reactor is cooled to room temperature; the reagents are then fed until the reactor is pressurized to 40 bars.

The reagent mixture consists of 1,2,4-trimethylbenzene, naphthalene and methanol, operating so as to have a molar ratio in the feeding between 1,2,4-trimethylbenzene and naphthalene equal to 10 and between methanol and naphthalene equal to 3.

When the pressure of 40 bars has been reached, the reactor is heated up to the test temperature of 350° C. The WSHV (hours$^{-1}$) (with respect to the total mixture) is 0.86. The products leaving the reactor are cooled and analyzed by means of gaschromatography. Samples are taken at regular time on stream intervals. The conversion of the methanol is always total.

In the case of the catalyst of example 1, the conversion of naphthalene after 49 hours is equal to 78.7%. The selectivities, with respect to naphthalene, are:

selectivity dimethylnaphtalenes (mole %): 48.3
selectivity 2,6-dimethylnaphthalene (mole %): 14.8
selectivity 2,6-1,6-1,5-dimethylnaphthalene (mole %): 30.3
selectivity methylnaphthalenes (mole %): 40.7
selectivity polymethylnaphthalenes (mole %): 11.0
ratio 2,6-dimethylnaphthalene/total dimethylnaphthalenes×100: 30.6
ratio 2,6-1,6-1,5-dimethylnaphthalene/total dimethylnaphthalenes×100: 62.8
ratio 2,6/2,7-dimethylnaphtalene: (thermodynamic about 1) 2.2

In the case of the catalyst obtained as in example 2, the conversion of naphthalene after 49 hours is equal to 76.1%.

The selectivities, with respect to naphthalene, are:
selectivity dimethylnaphtalenes (mole %): 47.0
selectivity 2,6-dimethylnaphthalene (mole %): 13.6
selectivity 2,6-1,6-1,5-dimethylnaphthalene (mole %): 28.7
selectivity methylnaphthalenes (mole %): 43.5
selectivity polymethylnaphthalenes (mole %): 9.5
ratio 2,6-dimethylnaphthalene/total dimethylnaphthalenes×100: 28.9
ratio 2,6-1,6-1,5-dimethylnaphthalene/total dimethylnaphthalenes×100: 61.0
ratio 2,6/2,7-dimethylnaphtalene: 1.9

In the case of the catalyst of example 1, the conversion of naphthalene after 74 hours is equal to 72.3%.

The selectivities, with respect to naphthalene, are:
selectivity dimethylnaphtalenes (mole %): 44.4
selectivity 2,6-dimethylnaphthalene (mole %): 13.4
selectivity 2,6-1,6-1,5dimethylnaphthalene (mole %): 27.6
selectivity methylnaphthalenes (mole %): 46.7
selectivity polymethylnaphthalenes (mole %): 8.8
ratio 2,6-dimethylnaphthalene/total dimethylnaphthalenes×100: 30.1
ratio 2,6-1,6-1,5-dimethylnaphthalene/total dimethylnaphthalenes×100: 62.1
ratio 2,6/2,7-dimethylnaphtalene: 2.2

In the case of the catalyst obtained as in example 2, the conversion of naphthalene after 74 hours is equal to 56.3%.

The selectivities, with respect to naphthalene, are:
selectivity dimethylnaphtalenes (mole %): 36.2
selectivity 2,6-dimethylnaphthalene (mole %): 10.5
selectivity 2,6-1,6-1,5dimethylnaphthalene (mole %): 22.0
selectivity methylnaphthalenes (mole %): 59.5
selectivity polymethylnaphthalenes (mole %): 4.3
ratio 2,6-dimethylnaphthalene/total dimethylnaphthalenes×100: 29.1
ratio 2,6-1,6-1,5-dimethylnaphthalene/total dimethylnaphthalenes×100: 60.7
ratio 2,6/2,7-dimethylnaphtalene: 2.0

In the case of the catalyst of example 1, the conversion of naphthalene after 95 hours is equal to 67.2%.

The selectivities, with respect to naphthalene, are:
selectivity dimethylnaphtalenes (mole %): 41.1
selectivity 2,6-dimethylnaphthalene (mole %): 12.2
selectivity 2,6-1,6-1,5dimethylnaphthalene (mole %): 25.3
selectivity methylnaphthalenes (mole %): 51.1
selectivity polymethylnaphthalenes (mole %): 7.7
ratio 2,6-dimethylnaphthalene/total dimethylnaphthalenes×100: 29.7
ratio 2,6-1,6-1,5-dimethylnaphthalene/total dimethylnaphthalenes×100: 61.4
ratio 2,6/2,7-dimethylnaphtalene: 2.2

In the case of the catalyst obtained as in example 2, the conversion of naphthalene after 95 hours is equal to 50.8%.

The selectivities, with respect to naphthalene, are:
selectivity dimethylnaphtalenes (mole %): 32.5
selectivity 2,6-dimethylnaphthalene (mole %): 9.0
selectivity 2,6-1,6-1,5dimethylnaphthalene (mole %): 18.6
selectivity methylnaphthalenes (mole %): 64.6
selectivity polymethylnaphthalenes (mole %): 2.9
ratio 2,6-dimethylnaphthalene/total dimethylnaphthalenes×100: 27.5
ratio 2,6-1,6-1,5-dimethylnaphthalene/total dimethylnaphthalenes×100: 57.2
ratio 2,6/2,7-dimethylnaphtalene: 2.0

It can therefore be seen that the catalytic composition of the present invention, at the beginning of the test, has an activity similar to that of the catalyst containing MTW zeolite alone. Subsequently, with an increase in the reaction time, the catalyst containing phosphorous has a much lower loss in activity and consequently a greater productivity.

In addition, as far as the product distribution is concerned, the modified catalyst allows more 2,6-dimethylnaphthalene to be obtained with respect to the total dimethylnaphthalenes, as also more 1,6 and 1,5-dimethylnaphthalene, isomers correlated to 2,6 by means of simple internal isomerization (α-β shift of the methyl on the naphthalene ring). In fact, it is well known that the 10 isomers of dimethylnaphthalene can be subdivided into four groups: A) 2,6-1,6-1,5; B) 2,7-1,7-1,8; C) 2,3-1,3-1,4; D) 1,2. The internal isomerization reaction takes place within these groups by simple α-β shift of the methyl. The same reaction, on the contrary, is extremely difficult between the above groups as it involves a β-β shift of the methyl between two adjacent positions, or its transfer between two different rings (see EP 051,9165, page 2 or N. Hara and H. Takahashi, Zeolite: Fundamental and Application, Kodansya Scientific, Tokyo, 1975, page 287).

The 2,6/2,7-DMN ratio which, as indicated in the description, has an important role with respect to the yield in the separation of the pure 2,6 isomer, is greater in the case of the catalyst with phosphorous. This is therefore another advantageous aspect of the present invention.

EXAMPLE 4

Preparation of a Composition Containing MTW Zeolite and 3% of P 2.4 grams of sodium aluminate at 56% of $Al_2O_3$ are dissolved in 84 grams of aqueous solution of tetraethylammonium hydroxide at 35%. The limpid solution thus obtained is poured, under stirring, into 200 grams of colloidal silica Ludox HS 40. After brief stirring, a limpid, homogeneous gel is obtained, which is poured into an AISI316 steel autoclave, equipped with an anchor stirrer. The gel is left to crystallize under hydrothermal conditions at 160° C. for about 60 hours.

At this point the autoclave is cooled and the solid separated from the mother liquor and washed with demineralized water until the washing water has a pH of less than 9.

The solid is calcined at 550° C. in an atmosphere of air for 5 hours. It is then suspended in a solution of demineralized water and ammonium acetate, the latter in an excess molar quantity, in particular 5 times, with respect to the synthesis aluminum formally present. During this operation, the synthesis sodium present in the zeolite is substituted by the ammonium ion by means of ion exchange. This first exchange is followed by a washing, a second exchange using the same procedure as the first and another washing. The solid is then definitively separated from the aqueous environment and dried, obtaining the zeolite in ammonia form. 10 grams of zeolite in ammonia form are dispersed in 50 grams of demineralized water in which $(NH_4)_2HPO_4$ has been dissolved in a ratio of 3% of P with respect to the zeolite, i.e. 1.29 g of salt. The mixture is maintained under stirring for about 30 minutes at approximately 60° C., and is then dried under vacuum. The solid thus obtained is calcined in air for 5 hours at 550° C., thus obtaining the catalyst in completely acid form.

An XRD analysis is carried out on the end-samples, demonstrating the presence of the crystalline MTW-type zeolitic phase alone, together with a chemical analysis on the basis of which the residual sodium proves to be less than 50 ppm and the molar ratio $SiO_2/Al_2O_3$ is 99.

EXAMPLE 5

Four grams of catalyst obtained as described in example 4, transformed into tablets and granulated within a range of 20–40 mesh, are charged into the isothermal zone of a fixed bed reactor, with quartz above and below as inert filler. The temperature of the reactor is brought to 200° C. for at least two hours, under a stream of nitrogen against atmospheric pressure. The reactor, maintained under a stream of inert gas, is cooled to room temperature; the reagents are then fed until the reactor is pressurized to 40 bars.

The reagent mixture consists of 1,2,4-trimethylbenzene, naphthalene and methanol, operating so as to have a molar ratio in the feeding between 1,2,4-trimethylbenzene and naphthalene equal to 10 and between methanol and naphthalene equal to 3.

When the pressure of 40 bars has been reached, the reactor is heated up to the test temperature of 350° C. The WSHV (hours$^{-1}$) (with respect to the total mixture) is 0.86. The products leaving the reactor are cooled and analyzed by means of gaschromatography. Samples are taken at regular time on stream intervals. The methanol conversion is always total.

The naphthalene conversion after 25 hours is equal to 11.8%.

The selectivities, with respect to naphthalene, are:
- selectivity dimethylnaphthalenes (mole %): 10.3
- selectivity 2,6-dimethylnaphthalene (mole %): 1.3
- selectivity 2,6-1,6-1,5dimethylnaphthalene (mole %): 3.7
- selectivity methylnaphthalenes (mole %): 89.7
- selectivity polymethylnaphthalenes (mole %): 0.0
- ratio 2,6-dimethylnaphthalene/total dimethylnaphthalenes×100: 12.5
- ratio 2,6-1,6-1,5-dimethylnaphthalene/total dimethylnaphthalenes×100: 35.6
- ratio 2,6/2,7-dimethylnaphthalene: (thermodynamic about 1) 2.0

As can be seen from the above data, the greater quantity of phosphorous has made the catalyst less active and less selective, as indicated, for example, by the 2,6-dimethylnaphthalene/total dimethylnaphthalene ratio.

EXAMPLE 6

Two catalytic tests are carried out analogously with the same reagents, using charges deriving from FOK.

Four grams of catalyst obtained as described in examples 1 and 2 respectively, transformed into tablets and granulated within a range of 20–40 mesh, are charged into the isothermal zone of a fixed bed reactor, with quartz above and below as inert filler. The temperature of the reactor is brought to 200° C. for at least two hours, under a stream of nitrogen against atmospheric pressure. The reactor, maintained under a stream of inert gas, is cooled to room temperature; the reagents are then fed until the reactor is pressurized to 40 bars.

The reagent mixture consists of 1,2,4-trimethylbenzene and a FOK distillate containing naphthalene, methylnaphthalenes, a few dimethylnaphthalenes, operating so as to have a molar ratio in the feeding between 1,2,4-trimethylbenzene and the naphthalene groups equal to 10. In particular, the naphthalene groups are divided as follows: 45.4% (by weight) naphthalene, 53.0% methylnaphthalenes, 1.6% dimethylnaphthalenes.

In order to prolong the life of the catalyst, before being fed to the reactor where the synthesis of 2,6-dimethylnaphthalene takes place, the feeding itself is pretreated with an acid montmorillonite (clay) in a quantity of 3% by weight with respect to the liquid phase. In this case, the operation was carried out batchwise for 5 hours at 80° C. After separating the montmorillonite from the liquid, the latter is fed to the reactor containing the catalyst activated in nitrogen, until the system is brought to the operating pressure, i.e. 40 bars. At this point the reactor is heated to the desired temperature of 350° C.

In this test, the state of the reagents and products is, therefore, under liquid phase conditions. The WHSV (hours$^{-1}$) (with respect to the total mixture) is 2. The products leaving the reactor are cooled and analyzed by means of gaschromatography. Samples are taken at regular time on stream intervals.

The following lists indicate (in weight %) the distributions of the naphthalene products, thus solvent free, in the two cases, with modified and non-modified catalyst, with different t.o.s.

In the case of the catalyst prepared as in example 1, i.e. modified, after 51 hours of reaction, the mixture of products, solvent free, has the following composition, expressed in weight % (the value relating to the feeding is indicated in brackets):
- naphthalene: 8.9 (45.4)
- 1-methylnaphthalene: 9.2 (20.4)
- 2-methylnaphthalene: 20.9 (32.6)
- 2,6-dimethylnaphthalene: 16.9 (0.0)
- 2,7-dimethylnaphthalene: 6.0 (1.6)
- 1,3-1,7-dimethylnaphthalene: 7.0 (0.0)
- 1,6-dimethylnaphthalene: 15.4 (0.0)
- 1,4-2,3-dimethylnaphthalene: 1.1 (0.0)
- 1,5-dimethylnaphthalene: 2.5 (0.0)
- 1,2-dimethylnaphthalene: 0.8 (0.0)
- 1,8-dimethylnaphthalene: 0.0 (0.0)
- trimethylnaphthalenes (various isomers): 11.3 (0.0)
- ratio 2,6-dimethylnaphthalene/total dimethylnaphthalenes×100: 34.0
- ratio 2,6+1,6+1,5-dimethylnaphthalene/total dimethylnaphthalenes×100: 70.0
- ratio 2,6/2,7-dimethylnaphthalene: 2.8

In the case of the catalyst prepared as in example 2, after 51 hours of reaction, the mixture of products, solvent free, has the following composition, expressed in weight % (the value relating to the feeding is indicated in brackets):
naphthalene: 9.3 (45.4)
1-methylnaphthalene: 9.4 (20.4)
2-methylnaphthalene: 21.4 (32.6)
2,6-dimethylnaphthalene: 15.5 (0.0)
2,7-dimethylnaphthalene: 6.5 (1.6)
1,3-1,7-dimethylnaphthalene: 7.8 (0.0)
1,6-dimethylnaphthalene: 13.8 (0.0)
1,4-2,3-dimethylnaphthalene: 1.1 (0.0)
1,5-dimethylnaphthalene: 2.3 (0.0)
1,2-dimethylnaphthalene: 0.8 (0.0)
1,8-dimethylnaphthalene: 0.0 (0.0)
trimethylnaphthalenes (various isomers): 12.1 (0.0)
ratio 2,6-dimethylnaphthalene/total dimethylnaphthalenes× 100: 32.4
ratio 2,6+1,6+1,5-dimethylnaphthalene/total dimethylnaphthalenes×100: 66.1
ratio 2,6/2,7-dimethylnaphthalene: 2.4

In the case of the catalyst prepared as in example 1, after 148 hours of reaction, the mixture of products, solvent free, has the following composition, expressed in weight % (the value relating to the feeding is indicated in brackets):
naphthalene: 11.2 (45.4)
1-methylnaphthalene: 10.4 (20.4)
2-methylnaphthalene: 23.3 (32.6)
2,6-dimethylnaphthalene: 16.0 (0.0)
2,7-dimethylnaphthalene: 5.7 (1.6)
1,3-1,7-dimethylnaphthalene: 6.6 (0.0)
1,6-dimethylnaphthalene: 14.4 (0.0)
1,4-2,3-dimethylnaphthalene: 1.1 (0.0)
1,5-dimethylnaphthalene: 2.3 (0.0)
1,2-dimethylnaphthalene: 0.8 (0.0)
1,8-dimethylnaphthalene: 0.0 (0.0)
trimethylnaphthalenes (various isomers): 8.2 (0.0)
ratio 2,6-dimethylnaphthalene/total dimethylnaphthalenes× 100: 34.2
ratio 2,6+1,6+1,5-dimethylnaphthalene/total dimethylnaphthalenes×100: 69.7
ratio 2,6/2,7-dimethylnaphthalene: 2.8

In the case of the catalyst prepared as in example 2, after 148 hours of reaction, the mixture of products, solvent free, has the following composition, expressed in weight % (the value relating to the feeding is indicated in brackets):
naphthalene: 12.1 (45.4)
1-methylnaphthalene: 10.5 (20.4)
2-methylnaphthalene: 23.9 (32.6)
2,6-dimethylnaphthalene: 14.4 (0.0)
2,7-dimethylnaphthalene: 6.1 (1.6)
1,3-1,7-dimethylnaphthalene: 7.0 (0.0)
1,6-dimethylnaphthalene: 13.0 (0.0)
1,4-2,3-dimethylnaphthalene: 1.1 (0.0)
1,5-dimethylnaphthalene: 2.2 (0.0)
1,2-dimethylnaphthalene: 0.8 (0.0)
1,8-dimethylnaphthalene: 0.0 (0.0)
trimethylnaphthalenes (various isomers): 8.9 (0.0)
ratio 2,6-dimethylnaphthalene/total dimethylnaphthalenes× 100: 32.3
ratio 2,6+1,6+1,5-dimethylnaphthalene/total dimethylnaphthalenes×100: 66.4
ratio 2,6/2,7-dimethylnaphthalene: 2.4

These tests with a naphthalene charge from FOK confirm the differences found with pure commercial naphthalene for the two types of catalyst: with the catalyst containing phosphorous a spectrum of products richer in 2,6-DMN and in 2,6+1,6+1,5-DMN is therefore obtained, together with a greater 2,6/2,7 ratio.

It should also be noted that in the case of FOK charges, there is also a product distribution more centered on dimethylnaphthalenes when the catalyst with phosphorous is used: in fact, although there are more dimethylnaphthalenes among the products, there are fewer trimethylnaphthalenes and not more, as might be expected as a result of a greater methylation of the naphthalene substrate.

The invention claimed is:

1. A process for preparing 2,6-dimethylnaphthalene which comprises subjecting to isomerization 1,6 and/or 1,5-dimethylnaphthalenes, optionally mixed with other isomers of dimethylnaphthalene, by treating said compounds at a temperature ranging from 100 to 400° C., under at least partially liquid phase conditions, in the presence of a catalytic composition containing an MTW zeolite and one or more elements selected from P, Si, and B.

2. The process according to claim 1, wherein the temperature ranges from 120 to 250° C.

* * * * *